United States Patent
Yanagihara et al.

(10) Patent No.: US 9,464,889 B2
(45) Date of Patent: Oct. 11, 2016

(54) METHOD AND APPARATUS FOR MEASURING HARDENED SURFACE LAYER

(75) Inventors: Arisa Yanagihara, Tokyo (JP); Minoru Tagami, Tokyo (JP); Kenichiro Watanabe, Tokyo (JP); Yoshinori Ishida, Tokyo (JP)

(73) Assignee: IHI CORPORATION, Tokyo (JP)

( * ) Notice: Subject to any disclaimer, the term of this patent is extended or adjusted under 35 U.S.C. 154(b) by 732 days.

(21) Appl. No.: 13/822,555

(22) PCT Filed: Sep. 16, 2011

(86) PCT No.: PCT/JP2011/071192
§ 371 (c)(1),
(2), (4) Date: May 22, 2013

(87) PCT Pub. No.: WO2012/036258
PCT Pub. Date: Mar. 22, 2012

(65) Prior Publication Data
US 2013/0231884 A1    Sep. 5, 2013

(30) Foreign Application Priority Data
Sep. 16, 2010    (JP) ................. 2010-207975

(51) Int. Cl.
*G01N 29/07*    (2006.01)
*G01B 17/02*    (2006.01)
*G01N 29/44*    (2006.01)
*G01N 29/30*    (2006.01)

(52) U.S. Cl.
CPC ............ *G01B 17/025* (2013.01); *G01N 29/07* (2013.01); *G01N 29/30* (2013.01); *G01N 29/4436* (2013.01); *G01N 29/4454* (2013.01); *G01N 2291/0251* (2013.01); *G01N 2291/02854* (2013.01); *G01N 2291/048* (2013.01); *G01N 2291/0423* (2013.01); *G01N 2291/102* (2013.01)

(58) Field of Classification Search
CPC ...................................................... G01N 29/07
USPC ............................................................ 702/97
See application file for complete search history.

(56) References Cited

U.S. PATENT DOCUMENTS 5,005,420 A * 4/1991 Miyajima .......... G01N 29/0618
73/620
5,628,319 A    5/1997 Koch et al.

FOREIGN PATENT DOCUMENTS

| JP | 60-031009 A | 2/1985 |
|---|---|---|
| JP | 62-277554 A | 12/1987 |
| JP | 2003-329657 A | 11/2003 |
| JP | 2004-333388 A | 11/2004 |
| JP | 2008-256575 A | 10/2008 |

* cited by examiner

Primary Examiner — Bryan Bui
(74) Attorney, Agent, or Firm — Volpe and Koenig, P.C.

(57) ABSTRACT

A method comprises a calibration curve creation step in which a calibration curve is created on the basis of hardened surface layer depth. A destructive test is performed on one of two samples in pairs, and propagation time of a first peak of a first wave of waveform of a signal outputted with the other in pairs in a non-destructive test is determined, the samples in pairs being prepared such that carburization depth varies gradually from pair to pair. A waveform of a signal outputted with a to-be-inspected piece is obtained. The propagation time of a first peak of a first wave of the waveform of the signal output with the to-be-inspected piece is obtained, and the hardened surface layer depth of the to-be-inspected piece is obtained using the calibration curve, on the basis of the propagation time obtained with the to-be-inspected sample.

7 Claims, 7 Drawing Sheets

METHOD AND APPARATUS FOR MEASURING HARDENED SURFACE LAYER

TECHNICAL FIELD

The present invention relates to a method and an apparatus for measuring a hardened surface layer, specifically a method and an apparatus for measuring the depth of a hardened surface layer by transmitting a surface wave to propagate along the hardened surface layer.

BACKGROUND ART

As a common measure against decrease in strength and abrasion resistance that solid materials may experience when used in some environments, a hardened surface layer is formed in the solid materials. The depth of such hardened surface layer is a parameter relying on which the mechanical qualities, such as strength and abrasion resistant, of pieces made from those solid materials are evaluated.

The Vickers hardness test, which is a destructive test, is one of the conventionally-used methods for measuring the hardened surface layer depth. The Vickers hardness test, which cuts a to-be-inspected piece to measure the depth of a hardened surface layer, has drawbacks that it takes time and that it cannot be applied to a piece of a solid material intended to be actually used to form a product. Hence, a non-destructive method for measuring the hardened surface layer depth is demanded.

There is known a non-destructive test method using an ultrasonic wave, in which an ultrasonic wave is transmitted to propagate along the surface of a to-be-inspected piece and the depth of a hardened surface layer is measured relying on the rate of change of sound wave speed (patent document 1).

PRIOR ART DOCUMENT

Patent Document

Patent Document 1: JP 6-14026 B

SUMMARY OF THE INVENTION

Problems to be Solved by the Invention

In the technique disclosed in patent document 1, in order to calculate the rate of change of sound wave speed, time taken for an echo to rise from when an ultrasonic surface wave is transmitted is measured. The time taken for an echo to rise is, however, likely to be read with error by an operator, which may have adverse effect on calculation of the hardened surface layer depth from the time measured.

The present invention has been made to solve the above problems. An object of the present invention is provide a method and an apparatus for measuring hardened surface layer depth which enable the depth of a hardened surface layer to be calculated with reduced error.

Means for Solving the Problems

In order to achieve the above object, the invention is a method of measuring depth of a hardened surface layer of a to-be-inspected piece, comprising a calibration curve creation step in which pairs of samples of a material of which the to-be-inspected piece is made are prepared such that carburization depth varies gradually from pair to pair, one of two samples in each pair is subjected to a destructive test to measure hardened surface layer depth, the other of the two samples in each pair is subjected to a non-destructive test performed with a transmitter probe and a receiver probe placed on a surface of interest of the sample, wherein propagation times of first and second peaks of a first wave of waveform of a signal outputted by the receiver probe receiving a surface wave transmitted from the transmitter probe to propagate along the surface of the sample are measured, and a first calibration curve and a second calibration curve are created on the basis of hardened surface layer depths and, the first peak propagation time and the second peak propagation time, respectively, and stored in an arithmetic processing device; a waveform measurement step in which the to-be-inspected piece is subjected to the non-destructive test performed with the transmitter probe and the receiver probe placed on a surface of interest of the to-be-inspected piece to obtain waveform of a signal outputted by the receiver probe receiving a surface wave transmitted from the transmitter probe to propagate along the surface of the to-be-inspected piece; a propagation time obtaining step in which propagation times of first and second peaks of a first wave of the waveform of the signal obtained in the waveform measurement step are obtained; and a hardened layer depth estimation step in which a first hardened surface layer depth is calculated using the first calibration curve, on the basis of the first peak propagation time obtained with the to-be-inspected piece, a second hardened surface layer depth is calculated using the second calibration curve, on the basis of the second peak propagation time obtained with the to-be-inspected piece, and an estimated value of hardened surface layer depth of the to-be-inspected piece is determined by averaging the first and second hardened surface layer depths.

Preferably, the method is a method of the type recited in claim 1, wherein in the calibration curve creation step, in addition to the pairs of samples prepared such that carburization depth varies gradually from pair to pair, a standard sample of the same material having carburization depth 0 is prepared, the standard sample is subjected to the non-destructive test to obtain propagation times of first and second peaks of a first wave of waveform of a signal outputted by the receiver probe receiving a surface wave transmitted from the transmitter probe to propagate along a surface of interest of the standard sample, and a calibration curve is created on the basis of the hardened surface layer depths obtained by the destructive test and a difference between the propagation time obtained with the sample in each pair and the propagation time obtained with the standard sample, and in the hardened layer depth estimation step, the hardened surface layer depth of the to-be-inspected piece is calculated using the calibration curve, on the basis of a difference between the propagation time obtained with the to-be-inspected piece in the propagation time obtaining step and the propagation time obtained with the standard sample.

Preferably, the method is a method, wherein in the waveform measurement step, the waveform of the signal is obtained in the form of a series of points by sampling the signal at a predetermined sampling frequency, wherein the first peak is an average of two points on the first wave sampled close to the first peak, and the second peak is an average of two points on the first wave sampled close to the second peak.

Preferably, the method is a method, wherein the calibration curve is approximated by an exponential function whose coefficient of determination is greater than or equal to 0.9.

Preferebly, the method is a method, wherein in the propagation time obtaining step as well as the calibration curve creation step, a gate range is set to contain the first and second peaks.

The invention is an apparatus for measuring depth of a hardened surface layer of a to-be-inspected piece, comprising a transmitter probe for transmitting a surface wave to propagate along a surface of interest of the to-be-inspected piece; a receiver probe for outputting a signal by receiving the surface wave transmitted from the transmitter probe; a probe moving means for moving the transmitter probe and the receiver probe closer to or farther away from the to-be-inspected piece; a waveform measurement means for obtaining waveform of the signal outputted by the receiver probe in a non-destructive test performed with the transmitter probe and the receiver probe placed on the surface of interest of the to-be-inspected piece using the probe moving means; a propagation time obtaining means for obtaining at least propagation time of a first peak of a first wave of the waveform obtained by the waveform measurement means; a calibration curve creation means for creating a calibration curve on the basis of hardened surface layer depths obtained by a destructive test performed on one of two samples in pairs, and propagation times obtained by the non-destructive test performed on the other of the two samples in pairs, using the wave measurement means and the propagation time obtaining means, the samples in pairs being of a material of which the to-be-inspected piece is made and prepared such that carburization depth gradually varies from pair to pair; and a hardened surface layer depth estimation means for calculating the hardened surface layer depth of the to-be-inspected piece using the calibration curve created by the calibration curve creation means, on the basis of the propagation time obtained with the to-be-inspected piece by the propagation time obtaining means, wherein the calibration curve creation means measures propagation times of first and second peaks of a first wave of waveform of the signal outputted with each sample, respectively, and creates first and second calibration curves on the basis of the hardened surface layer depths and the first peak propagation times and on the basis of the hardened surface layer depths and the second peak propagation times, respectively, and stores the first and second calibration curves in an arithmetic processing device, and the propagation time obtaining means obtains propagation times of first and second peaks of a first wave of the waveform of the signal outputted with the to-be-inspected piece, obtained by the waveform measurement means respectively, and the hardened layer depth estimation means calculates a first hardened surface layer depth using the first calibration curve, on the basis of the first peak propagation time obtained with the to-be-inspected piece, and a second hardened surface layer depth using the second calibration curve, on the basis of the second peak propagation time obtained with the to-be-inspected piece, and determines an estimated value of hardened surface layer depth of the to-be-inspected piece by averaging the first and second hardened surface layer depths.

Preferably, the apparatus is an apparatus, wherein the calibration curve creating means creates a calibration curve on the basis of the hardened surface layer depths obtained by the destructive test performed on one of the two samples in each pair and a difference between propagation time obtained with the other of the two samples in each pair and propagation time obtained with a standard sample using the waveform measurement means and the propagation time obtaining means, the standard sample being of the same material as the samples in pairs and having carburization depth 0, and the hardened surface layer depth estimation means calculates the hardened surface layer depth of the to-be-inspected piece using the calibration curve, on the basis of a difference between the propagation time obtained with the to-be-inspected piece using the propagation time obtaining means and the propagation time obtained with the standard sample.

Advantageous Effects of the Invention

In the method of measuring the hardened surface layer depth according to the present invention, pairs of samples are prepared such that carburization depth varies gradually from pair to pair, one of two samples in each pair is subjected to the destructive test to measure hardened surface layer depth, and the other of the two samples in each pair is subjected to the non-destructive test performed with a transmitter probe and a receiver probe placed on a surface of interest of the sample to measure propagation times of first and second peaks of a first wave of waveform of a signal outputted by the receiver probe receiving a surface wave transmitted from the transmitter probe to propagate along the surface of the sample. On the basis of hardened surface layer depths and propagation times obtained, a calibration curve is created. Then, a to-be-inspected piece is subjected to the non-destructive test performed with the transmitter probe and the receiver probe placed on a surface of interest of the to be-inspected piece to obtain propagation time. Then, in the hardened layer depth estimation step, the hardened surface layer depth of the to-be-inspected piece is calculated using the calibration curve, on the basis of propagation times of first and second peaks of a first wave of waveform of a signal outputted with the to-be-inspected piece, obtained in the waveform measurement step.

In the apparatus for measuring the hardened surface layer depth according to the present invention, a to-be-inspected piece is subjected to a non-destructive test performed with the transmitter probe and the receiver probe placed on a surface of interest of the to-be-inspected piece to obtain propagation times of first and second peaks of a first wave of waveform of a signal, obtained by the waveform measurement means. A calibration curve is created on the basis of hardened surface layer depths obtained by a destructive test performed on one of two samples in pairs and propagation times obtained by the non-destructive test performed on the other of the two samples in pairs, using the wave measurement means and the propagation time obtaining means, the samples in pairs being prepared such that carburization depth gradually varies from pair to pair. Then, the hardened surface layer depth of the to-be-inspected piece is calculated using the calibration curve, on the basis of the propagation time obtained with the to-be-inspected piece.

The propagation times of first and second peaks of a first wave of waveform of a signal outputted with the to-be-inspected piece can be read with reduced error, leading to improved accuracy of the calculated hardened layer surface depth.

MODE FOR CARRYING OUT THE INVENTION

With reference to the drawings attached, embodiments of the present invention will be described.

Figure 1:
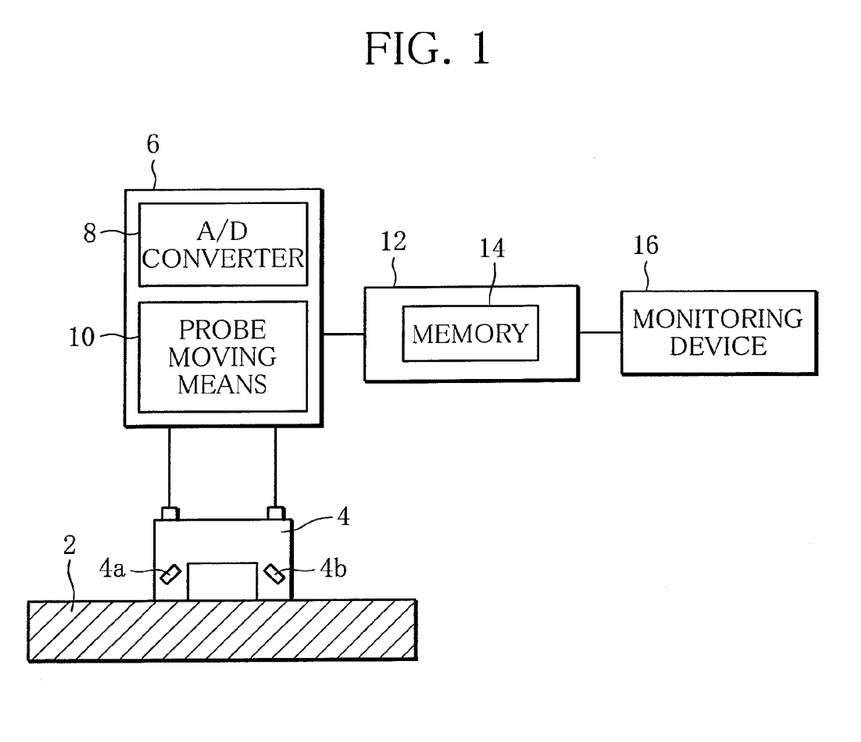
FIG. 1 is a diagram schematically showing the configuration of a hardened surface layer measurement apparatus according to the present invention.

FIG. 1 is a diagram schematically showing the configuration of a hardened surface layer measurement apparatus according to the present invention.

The hardened surface layer measurement apparatus 1 is intended to measure, for example the depth of a carburized hardened layer of a carburized solid material, to evaluate qualities, such as strength, of the solid material.

As shown in FIG. 1, the measurement apparatus 1 comprises a probe 4 including a transmitter probe for transmitting an ultrasonic wave to propagate along a surface of interest of a to-be-inspected piece 2 and a transmitted, the transmitter probe and the receiver probe being integrated, an ultrasonic wave measurement unit 6 connected to the probe 4, an arithmetic processing unit 12 for performing tasks, including processing of data obtained through the probe 4 and setting of the conditions of the probe's transmitting and receiving the ultrasonic wave, and a monitoring device 16 connected to the arithmetic processing unit 12.

The transmitter probe 4a and the receiver probe 4b, included in the probe 4, are arranged opposite to each other to transmit and receive an ultrasonic wave propagating along the surface of the to-be-inspected piece 2 with high sensitivity. The transmitter probe 4a and the receiver probe 4b are placed on the surface of the piece 2, a predetermined distance away from each other.

The ultrasonic measurement unit 6 includes a probe moving means 10 for moving the probe 4 nearer to or farther away from the surface of the piece 2. The arithmetic processing unit 12 controls the probe moving means 10.

The arithmetic processing unit 12 includes a central processing unit and memory 14 including RAM and ROM. Programs are stored in the memory 14. The programs include a gate setting program. If a gate, or time range is set, information including peak values of a signal within the set time range, and propagation times corresponding to those peak values is obtained automatically. The information automatically obtained can be monitored on the monitoring device 16, along with measurement data obtained.

Now, the method of measuring the hardened surface layer with the measurement apparatus 1 according to the present invention, configured as described above, will be described.

Figure 2:
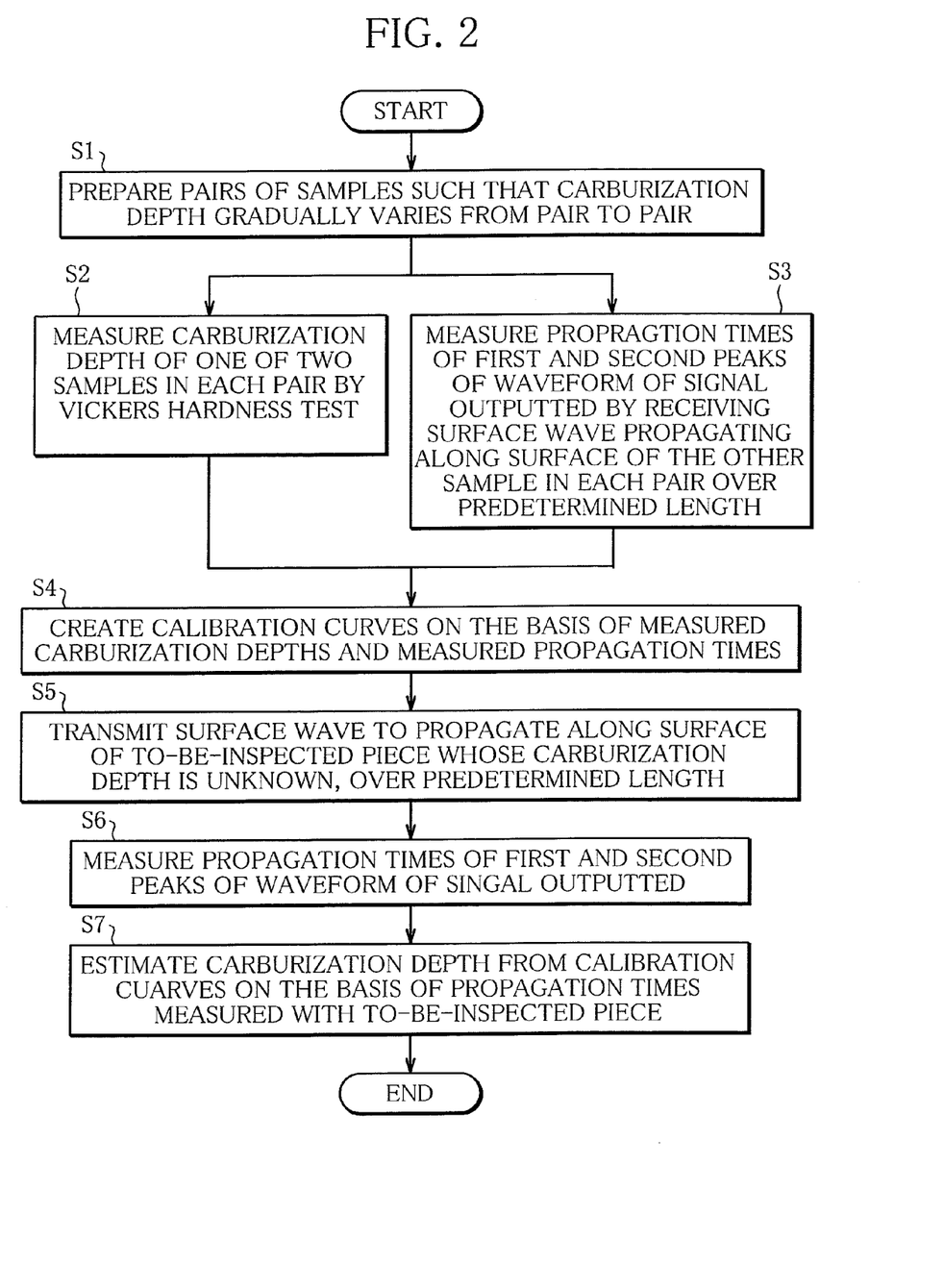
FIG. 2 is a flow chart showing a hardened surface layer measurement method.

FIG. 2 is a flow chart showing a hardened surface layer measurement method, or process of measuring the depth of carburization in a to-be-inspected piece 2. A description will be given following this flow chart.

In step S1, pairs of samples 2 of a material of which the to-be-inspected piece is made are prepared such that carburization depth gradually varies from pair to pair. One of two samples 2 in each pair is subjected to a destructive test, while the other is subjected to a non-destructive test. The two samples 2 in each pair, having the same carburization depth, are desirably prepared by being carburized together.

In step S2, the Vickers hardness test, which is a destructive test, is performed on one of the two samples 2 in each pair, specifically on a cross-section of the carburized layer thereof to measure the carburization depth thereof (calibration curve creation step).

In step S3, a non-destructive test is performed on the other of the two samples 2 in each pair by placing the probe 4 on a surface of interest of the sample 2. Specifically, with the probe 4 placed on each sample 2, an ultrasonic wave is transmitted to propagate along the surface of the sample 2 over a predetermined length (waveform measurement means), and propagation times of first and second peaks of waveform of a signal, outputted by the receiver probe receiving the ultrasonic wave, are measured, respectively (calibration curve creation step, propagation time obtaining means).

Figure 3:
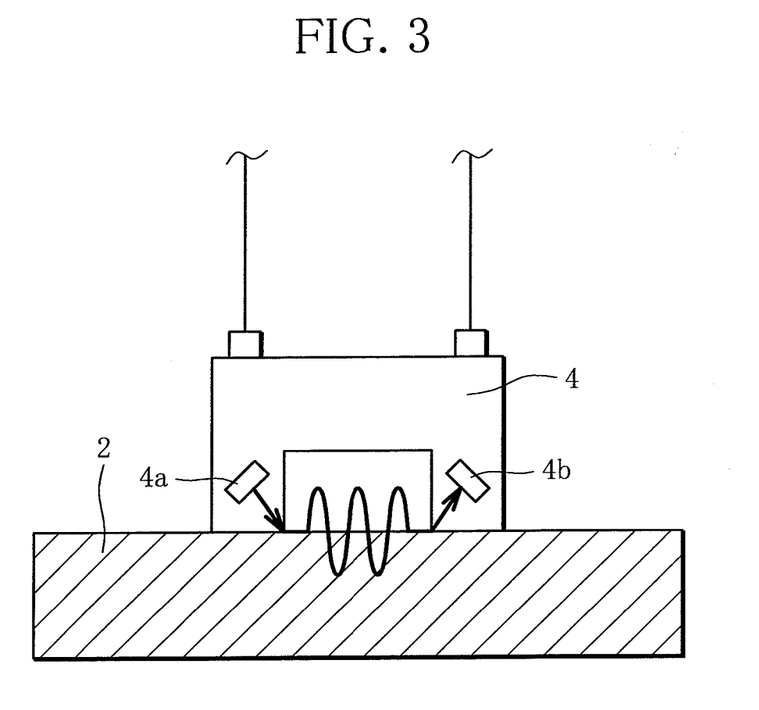
FIG. 3 is a diagram schematically showing a surface wave propagating along a surface of a sample, partly in an enlarged size.
Figure 4A:
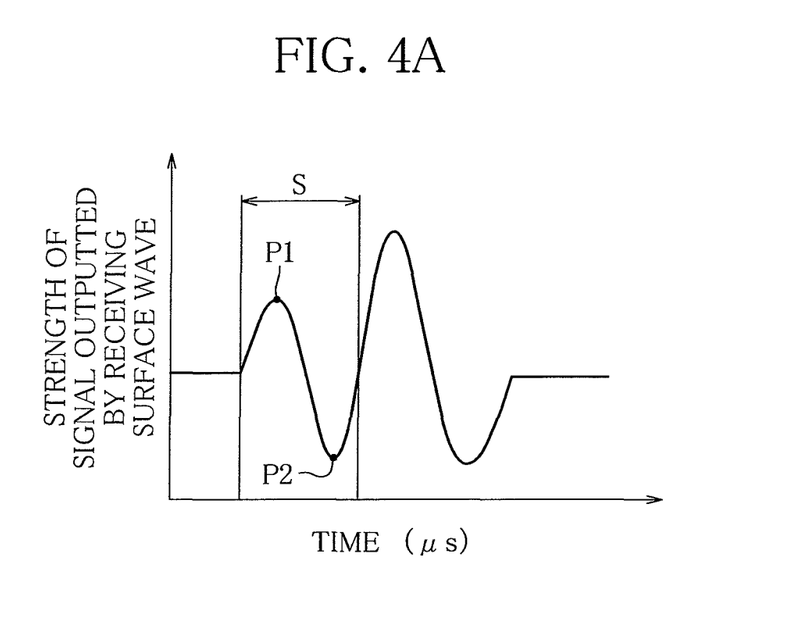
FIG. 4A is a diagram showing an example of a waveform of a signal outputted in an embodiment of the present invention.
Figure 4B:
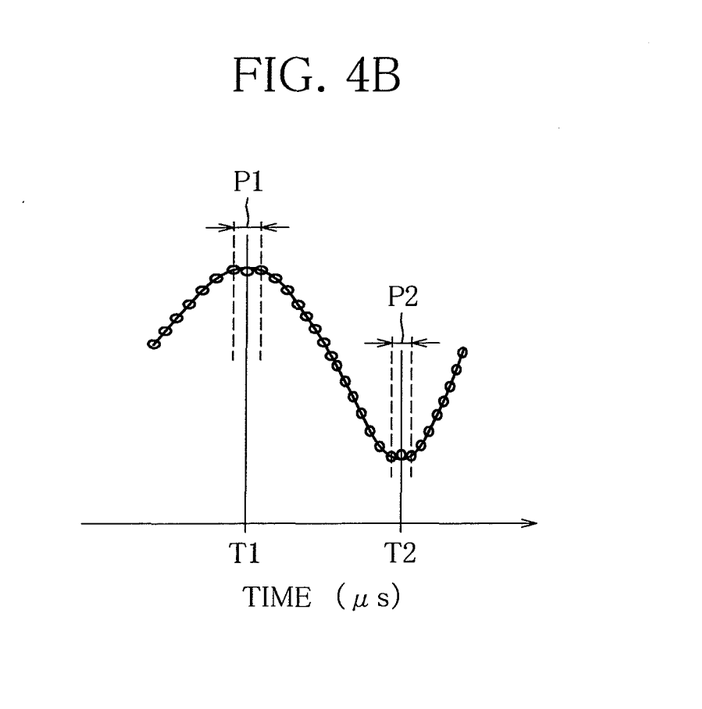
FIG. 4B is an enlarged diagram showing a gate range set as indicated in FIG. 4A.
Figure 5:
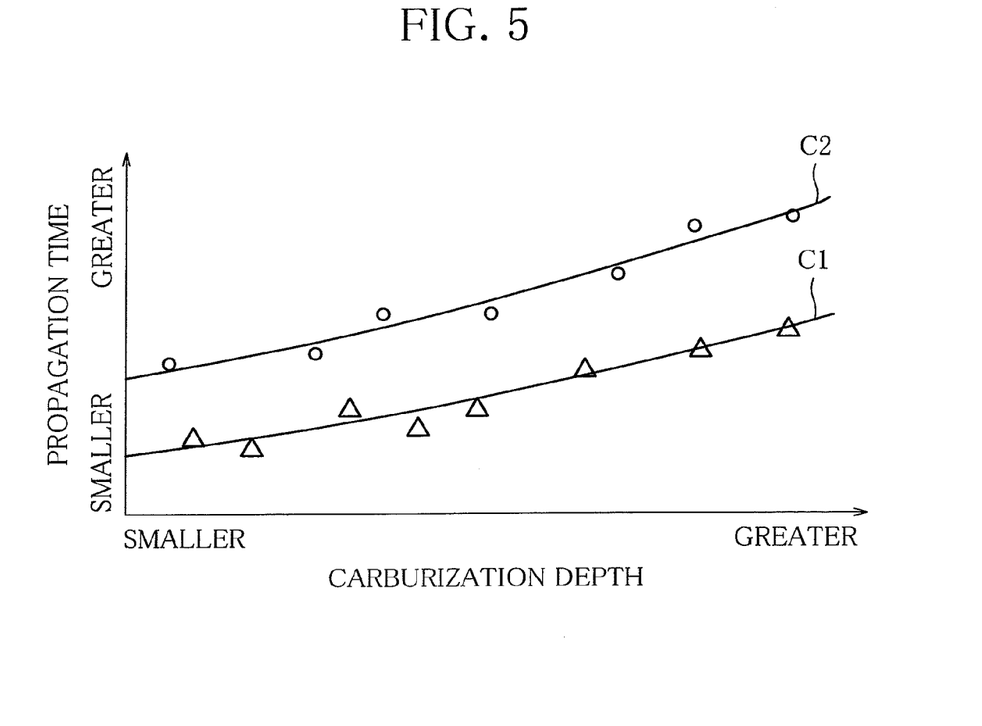
FIG. 5 is a graph showing examples of calibration curves created in the embodiment of the present invention.

With reference to FIGS. 3 to 5, a detailed description will be given.

FIG. 3 is a diagram schematically showing an ultrasonic wave propagating along the surface of a sample 2, partly in an enlarged size. The ultrasonic wave is transmitted from the transmitter probe 4a of the probe 4 to propagate along the surface of the sample 2 as a surface wave, and received by the receiver probe 4b.

FIG. 4A shows the waveform of a signal outputted by the receiver probe 4b receiving the surface wave.

As indicated in FIG. 4A, a gate range S is set by the arithmetic processing unit 12 to contain first and second peaks P1, P2 of a first wave of waveform of the signal. When the gate range S is set, maximum and minimum signal values within the gate range S and propagation times corresponding to the maximum and minimum values, respectively, are obtained automatically.

The waveform of the signal outputted by the receiver probe 4b receiving the surface wave is obtained in the form of a series of points by sampling the signal at regular intervals determined by the sampling frequency (predetermined sampling frequency) of an A/D converter (analogue/digital converter) 8, which means that a peak of the signal is not necessarily sampled.

Thus, as indicated in FIG. 4B which shows the gate range S of FIG. 4 in an enlarged size, propagation time corresponding to an average of signal strengths of two points sampled close to the first peak P1 is obtained as first peak P1 propagation time T1, and propagation time corresponding to an average of signal strengths of two points sampled close to the second peak P2 is obtained as second peak P2 propagation time T2.

Desirably, the A/D converter 8 is set at higher sampling frequency, since higher sampling frequency results in the signal being sampled at shorter intervals, and thus, a point closer to a peak of the signal being sampled. It is also possible to perform step S3 more than once and obtain propagation times T1 and T2 by averaging values obtained each time.

In subsequent step S4, calibration curves are created on the basis of actually-measured carburization depths, namely carburization depths measured in step S2 and propagation times obtained in step S3, and stored in the arithmetic processing unit 12 (calibration curve creation step, calibration curve creation means).

Specifically, first peak P1 propagation times T1 and second peak P2 propagation times T2 are plotted against actually-measured carburization depths, as seen in FIG. 5 which shows examples of calibration curves. Since the carburization causes exponential change in physical quantities, calibration curves are created using exponential functions such that the $R^2$ value, or coefficient of determination, which is a measure of how much the plotted points differ from the calibration curve, is 0.9 or greater. In FIG. 5, calibration curve C1 represents a relationship between first peak P1 propagation time T1 and carburization depth, and calibration curve C2 represents a relationship between second peak P2 propagation time T2 and carburization depth. Incidentally, calibration curves C1, C2 in FIG. 5 were created on the basis of data obtained with the A/D converter 8 set at the sampling frequency of 800 MHz, where step 3 was performed three times and an average of the values obtained each time was used as propagation time.

In subsequent step S5, using the probe 4, a surface wave is transmitted to propagate along a surface of interest of the to-be-inspected piece 2 whose carburization depth is unknown, over the predetermined length (waveform measurement step, waveform measurement means).

In step S6, propagation times T1, T2 of first and second peaks P1, P2 of waveform of a signal outputted in step S5 are measured, respectively (propagation time obtaining step, propagation time obtaining means).

Specifically, as in step S1, a gate range S is set by the arithmetic processing unit 12 to contain first and second peaks P1, P2 of a first wave of waveform of a signal so that maximum and minimum signal strengths within the gate range S, and propagation times T1, T2 corresponding to the maximum and minimum signal strengths, respectively, are obtained automatically. Specifically, as first peak P1 propagation time T1, propagation time corresponding to an average of signal strengths of two points sampled close to the first peak P1 is obtained. Likewise, as second peak P2 propagation time T2, propagation time corresponding to an average of signal strengths of two points sampled close to the second peak P2 is obtained.

In step S7, using the calibration curves, which have been stored in the arithmetic processing unit 12 in step S4, carburization depth is estimated on the basis of the first peak P1 propagation time T1 and the peak P2 propagation time T2 obtained in step S6 (hardened layer depth estimation step, hardened layer depth estimation means).

Specifically, the estimated value of carburization depth is determined by averaging a carburization depth corresponding to the first peak P1 propagation time T1 on the calibration curve C1, and a carburization depth corresponding to the second peak P2 propagation time T2 on the calibration curve C2.

The accuracy of the carburization depth estimated by the above-described method was inspected.

Using the calibration curves, the unknown carburization depth of a piece was estimated. The carburization depth estimated was 0.565 mm.

By the Vickers hardness test, the carburization depth of the same piece was measured. The carburization depth measured was 0.611 mm.

The error in the estimated value is 0.05 mm, which indicates that the carburization depth was estimated with high accuracy.

As explained above, in the present embodiment, pairs of samples 2 are prepared such that carburization depth gradually varies from pair to pair. One of two samples 2 in each pair is subjected to the Vickers hardness test to measure the carburization depth thereof, while the other in each pair is subjected to the non-destructive test to obtain propagation times T1, T2 of first and second peaks P1, P2 of a first wave of waveform of a signal outputted by receiving a surface wave propagating along the surface of the sample 2 over a predetermined length, respectively. On the basis of these actually-measured carburization depths and propagation times, calibration curves C2, C2 are created. Then, a to-be-inspected piece 2 whose carburization depth is unknown is subjected to the non-destructive test to obtain propagation times T1, T2 of first and second peaks P1, P2 of a first wave of waveform of a signal outputted by receiving a surface wave propagating along the surface of the to-be-inspected piece over the predetermined length, respectively. Then, using the calibration curves C1, C2, the carburization depth of the to-be-inspected piece is estimated on the basis of the first peak P1 propagation time T1 and second peak P2 propagation time T2 obtained with the to-be-inspected piece.

In the estimation of an unknown carburization depth of a to-be-inspected piece 2 as well as the creation of the calibration curves, propagation times T1, T2 of first and second peaks P1, P2 of a first wave of waveform of a signal outputted by receiving a surface wave propagating along the surface of the to-be-inspected piece or a sample over the predetermined length are measured. Such propagation times can be read with reduced error, leading to improved accuracy of the estimated carburization depth.

Creating the calibration curves on the basis of actually-measured carburization depths and propagation times obtained with pairs of samples 2 prepared such that carburization depth varies from pair to pair also leads to improved accuracy of the estimated carburization depth.

Determining the estimated value of carburization depth by averaging carburization depths obtained from the calibration curves C1, C2, respectively, leads to further improved accuracy of the estimated carburization depth.

The waveform of a signal is obtained in the form a series of points by sampling the signal with the A/D converter 8 at short intervals determined by sampling frequency, where propagation time corresponding to an average of signal strengths of two points sampled close to a first peak P1 is obtained and fed to the arithmetic processing unit 12 as first peak P1 propagation time T1, and propagation time corresponding to an average of signal strengths of two points sampled close to a second peak P2 is obtained and fed to the arithmetic processing unit 12 as second peak P2 propagation time T2. This means that propagation time of a point closer to the peak is obtained, leading to improved accuracy of the estimated carburization depth.

Setting a gate range S to contain first and second peaks P1, P2 so that propagation times T1, T2 will be automatically obtained leads to reduced error in the read propagation times T1, T2, and thus, improved accuracy of the estimated carburization depth. This also shortens the time taken to estimate the carburization depth.

Carburization causes exponential change in physical quantities. Thus, calibration curves C1, C2 are created using exponential functions approximating the relationship between propagation time and actually-measured carburization depth such that the coefficient of determination with regard to plots of propagation time against actually-measured carburization depth is greater than or equal to 0.9. Use of the exponential functions approximating the relationship between propagation time and actually-measured carburization depth at such a high level greatly reduces error in the estimated carburization depth, and shortens the time taken to estimate the carburization depth.

<Variant>

A variant of the above-described embodiment will be described below. The variant is different from the above embodiment in that carburization depth is estimated using calibration curves created using a standard sample; in other respects, both are similar. The description of the features shared by both will be omitted.

Figure 6:
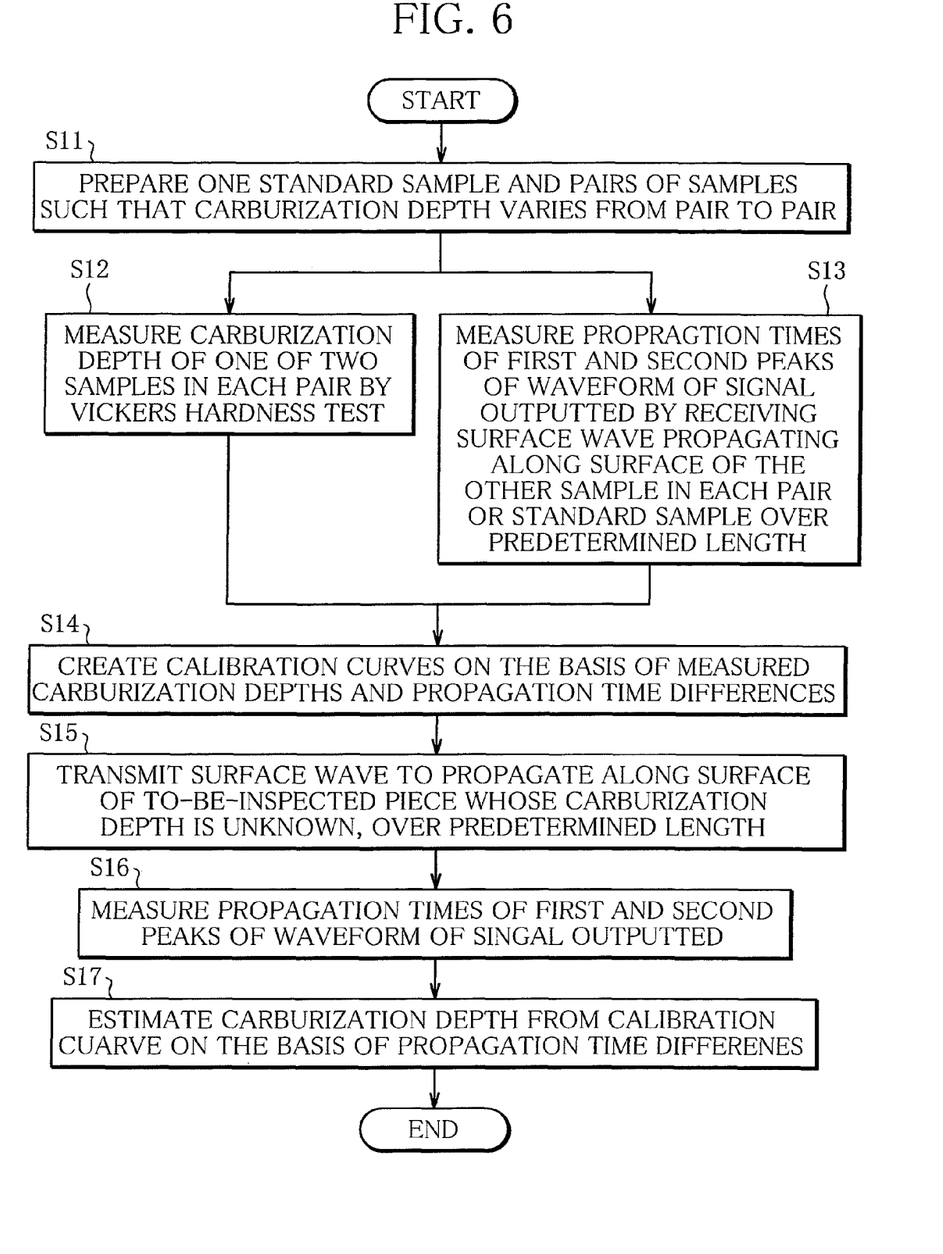
FIG. 6 is a flow chart showing a variant of measurement method according to the present invention.

FIG. 6 is a flow chart showing a hardened surface layer measurement method, according to which, the variant will be described.

In step S11, in addition to pairs of samples 2 prepared such that carburization depth gradually varies from pair to pair, a standard sample 2 is prepared. The standard sample is of the same solid material as the samples 2 prepared in pairs, but has experienced another heat treatment process than carburization.

More specifically, the standard sample is a sample having experienced another heat treatment process than the carburization and diffusion process causing carbon to diffuse into the solid material, and thus, has a carburization depth 0. Here, the heat treatment process other than the carburization and diffusion process may be, for example, heating, quenching, deep cooling or tempering.

The reason for use of a heat-treated standard sample is that solid materials having experienced a heat treatment exhibit greatly different characteristics as compared with those not having experienced a heat treatment. Since the characteristics of heat-treated materials vary depending on heating/cooling temperature, the standard sample is desirably prepared through a heat treatment performed on similar conditions to those on which the samples 2 in pairs are prepared by carburization.

In step S12, the Vickers hardness test, which is a destructive test, is performed on one of two samples 2 in pairs prepared such that carburization depth gradually varies from pair to pair, specifically on a cross-section of the carburized layer thereof to measure the carburization depth thereof (calibration curve creation step).

In subsequent step S13, propagation time measurement, which is a non-destructive test, is performed on the standard sample as well as the other of the two samples 2 in each pair (calibration curve creation step, propagation time obtaining means). The propagation time measurement is performed in the same way as in step S3. Specifically, with the probe 4 placed on a surface of interest of the standard sample, an ultrasonic wave is transmitted to propagate along the surface of the standard sample over a predetermined length, and propagation times of first and second peaks of waveform of a signal outputted by receiving the ultrasonic wave are measured, respectively.

The propagation time measurement is performed on the sample 2 in each pair in the same way.

In step S14, calibration curves are created on the basis of actually-measured carburization depths, namely carburization depths measured with the sample 2 in each pair in step S12 and propagation times obtained with the standard sample and the sample 2 in each pair in step S13, and stored in the arithmetic processing unit 12 (calibration curve creation step, calibration curve creation means).

Specifically, a difference between the first peak propagation time obtained with the sample 2 in each pair and the first peak propagation time obtained with the standard sample as well as a difference between the second peak propagation time obtained with the sample 2 in each pair and the second peak propagation time obtained with the standard sample is plotted against actually-measured carburization depths, upon which calibration curves are created.

Figure 7:
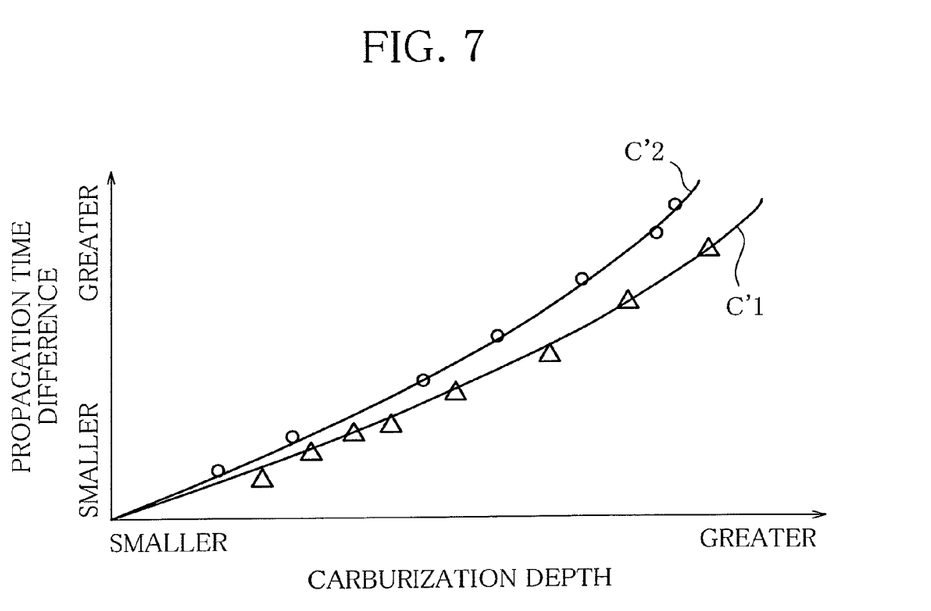
FIG. 7 is a graph showing examples of calibration curves created in the variant of the present invention.

As seen in FIG. 7 which shows examples of calibration curves, first peak propagation time differences as well as second peak propagation time differences are plotted against actually-measured carburization depths. In FIG. 7, calibration curve C'1 represents a relationship between first peak propagation time difference and carburization depth, and calibration curve C'2 represents a relationship between second peak propagation time difference and carburization depth. Incidentally, calibration curves C'1, C'2 in FIG. 7 were created on the basis of data obtained with the A/D converter 8 set at the sampling frequency of 6 MHz.

Referring back to FIG. 6, in step S5, using the probe 4, a surface wave is transmitted to propagate along a surface of interest of a to-be-inspected piece 2 whose carburization depth is unknown, over the predetermined length (waveform measurement step, waveform measurement means).

In step S16, propagation times T1, T2 of first and second peaks P1, P2 of waveform of a signal outputted in step S15 are measured, respectively (propagation time obtaining step, propagation time obtaining means).

In step S17, using the calibration curves created in step S14, the unknown carburization depth of the to-be-inspected piece 2 is estimated on the basis of the first peak P1 propagation time T1 and the second peak P2 propagation time T2 obtained with the to-be-inspected piece in steps S15, S16 (hardened layer depth estimation step, hardened layer depth estimation means).

Specifically, a propagation time difference dT1 is obtained from the first peak propagation time obtained with the to-be-inspected piece 2 in step S16 and the first peak propagation time obtained with the standard sample in step 13, and a propagation time difference dT2 is obtained from the second peak propagation time obtained with the to-be-inspected piece 2 and the second peak propagation time obtained with the standard sample. Then, carburization depths corresponding to the propagation time differences dT1, dT2 on calibration curves C'1, C'2, respectively, are obtained. The estimated value of the unknown carburization depth of the to-be-inspected piece 2 is determined by averaging the two carburization depths obtained.

The accuracy of the carburization depth estimated by the above-described method was inspected.

Using the calibration curves C'1, C'2 created in the above-described manner, the unknown carburization depth of a piece was estimated. The carburization depth estimated was 0.465 mm. By the Vickers hardness test, the carburization depth of the same piece was measured. The carburization depth measured was 0.486 mm. The error in the estimated value is −0.02 mm, which indicates that the carburization depth was estimated with high accuracy.

As explained above, in the present embodiment, calibration curves C'1, C'2 are created on the basis of propagation time difference between the standard sample and the sample 2 in each of pairs prepared such that carburization depth varies from pair to pair and actually-measured carburization depth of the sample 2 in each of the pairs. Then a first peak propagation time difference and a second peak propagation time difference between the standard sample and a to-be-inspected piece whose carburization depth is unknown are obtained, and carburization depths corresponding to the obtained first and second peak propagation time differences on the calibration curves C'1, C'2, respectively, are obtained.

The carburization depth is estimated using the calibration curves created on the basis of a difference in propagation time observed between the standard sample and the sample in each of pairs, and thus, using the propagation time obtained with the standard sample as a base. This way of estimation has an advantage that the influence of sample 2 measurement conditions, such as temperature at which samples 2 are produced, and an operator who measures the carburization depth of samples 2, is reduced, leading to improved accuracy of the estimated carburization depth.

This obviates a need to correct the estimated value to compensate for the influence of the measurement conditions, and thus, provides increased ease of carburization depth estimation.

In order to estimate the carburization depth of a to-be-inspected piece which is made of basically the same solid material as the samples but different in type, specifically different in alloy-forming element added, the present embodiment, designed to estimate carburization depth on the basis of a propagation time difference between the standard sample and a to-be-inspected piece 2, can be modified to make correction to the carburization depth estimated from the calibration curve.

Next, this variant will be described, where the type of the samples will be called "type A", and the type which is basically the same solid material but distinct from type A will be called "type B".

If the unknown carburization depth of a to-be-inspected piece 2b of type B is estimated using calibrations curves Cn1, Cn2 created on the basis of first peak propagation times and second peak propagation times obtained with the type A standard sample and the type A samples 2a in pairs, error in the estimated carburization depth is great because the types are different. To deal with this, zero point adjustment is performed on carburization depths of the to-be-inspected piece 2 estimated from the calibration curves Cn1, Cn2, respectively.

The zero point adjustment is a procedure in which a standard sample of type B is prepared, first peak propagation time Tb1 and second peak propagation time Tb2 are measured with the type B standard sample, and correction quantities to compensate for deviations of the first and second peak propagation times Tb1, Tb2 from the first and second peak propagation times Ta1, Ta2 measured with the type A standard sample are obtained. Let us suppose that the first peak propagation time Ta1 measured with the type A standard sample is 20 μs while the first peak propagation time Tb1 measured with the type B standard sample is 21 μs. The deviation of the propagation times Tb1 from the propagation time Ta1 is 1 μs, and thus, the correction quantity to compensate for the deviation is 1 μs. Thus, the first peak propagation time measured with a to-be-inspected piece of type B is corrected with the correction quantity of 1 μs, and carburization depth corresponding to the first peak propagation time thus corrected is estimated from the calibration curve Cn1. Let us suppose that the second peak propagation time Ta2 measured with the type A standard sample is 40 μs while the second peak propagation time Tb2 measured with the type B standard sample is 42 μs. The deviation of the propagation time Tb2 from the propagation time Ta2 is 2 μs, and thus, the correction quantity to compensate for the deviation is 2 μs. Thus, the second peak propagation time measured with the to-be-inspected piece of type B is corrected with the correction quantity of 2 μs, and carburization depth corresponding to the second peak propagation time thus corrected is estimated from the calibration curve Cn2.

According to this method, the unknown carburization depth of a piece was estimated using calibrations curves created using samples of another type.

Specifically, the unknown carburization depth of a piece 2d of type D was estimated using calibration curves created on the basis of propagation times measured with a standard sample of type C and samples in pairs of type C. The carburization depth of the piece 2d estimated not through the zero point adjustment was 0.652 mm. The carburization depth of the piece 2d estimated through the zero point adjustment was 0.535 mm, and the carburization depth of the piece 2d actually measured was 0.487 mm. The error in the estimated value is thus 0.05 mm, which indicates that the carburization depth of even a piece of another type was estimated with high accuracy through the zero point adjustment.

As seen from the above, the carburization depth of pieces which are made basically of the same solid material but different in type from those samples on which the calibration curves are based can be estimated with high accuracy from the same calibrations curves, by preparing a standard sample of each type, obtaining a correction quantity to compensate for a deviation in propagation time using the standard sample of each type, and making zero point adjustment using the correction quantity obtained.

In the above, embodiments of the present invention have been described. The present embodiment is however not restricted to the described embodiments.

For example, in the described embodiments, in creation of calibration curves C1, C2 as well as in estimation of the unknown carburization depth of a to-be-inspected piece 2, propagation times of first and second peaks P1, P2 of waveform of a signal outputted by receiving a surface wave propagating along the surface of a sample 2 or a to-be-inspected piece 2 are obtained, respectively. It may however be modified such that only the propagation time of the first peak of the first wave is obtained, and that the carburization depth is estimated from only the calibration curve C1 created on the basis of first peak propagation times.

Although the embodiments have been described taking estimation of carburization depth as an example, the application of the present invention is not restricted to it; the present invention has applications including measurement of the depth of hardened layers other than the carburized layer, and measurement of the thickness of metal coating.

In the above-described embodiments, the calibration curve for use in carburization depth estimation relates propagation time or propagation time difference to carburization depth. Another parameter may, however, be related to the carburization depth. For example, rate of change of propagation time, sound wave speed, rate of change of sound wave speed, or sound wave speed difference may be related to the carburization depth.

EXPLANATION OF REFERENCE SIGNS

1 Measurement apparatus
4 Probe
6 Ultrasonic wave measurement unit
8 A/D converter
10 Probe moving means
12 Arithmetic processing unit
14 Memory

The invention claimed is:
1. A method of measuring depth of a hardened surface layer of a to-be-inspected piece, comprising:
 a calibration curve creation step in which pairs of samples of a material of which the to-be-inspected piece is made are prepared such that carburization depth varies gradually from pair to pair, one of two samples in each pair is subjected to a destructive test to measure hardened surface layer depth, the other of the two samples in each pair is subjected to a non-destructive test per- formed with a transmitter probe and a receiver probe placed on a surface of interest of the sample, wherein propagation times of first and second peaks of a first wave of waveform of a signal outputted by the receiver probe receiving a surface wave transmitted from the transmitter probe to propagate along the surface of the sample are measured, and a first calibration curve and a second calibration curve are created on the basis of hardened surface layer depths and, the first peak propagation time and the second peak propagation time, respectively, and stored in an arithmetic processing device;

a waveform measurement step in which the to-be-inspected piece is subjected to the non-destructive test performed with the transmitter probe and the receiver probe placed on a surface of interest of the to-be-inspected piece to obtain waveform of a signal outputted by the receiver probe receiving a surface wave transmitted from the transmitter probe to propagate along the surface of the to-be-inspected piece;

a propagation time obtaining step in which propagation times of first and second peaks of a first wave of the waveform of the signal obtained in the waveform measurement step are obtained; and a hardened layer depth estimation step in which a first hardened surface layer depth is calculated using the first calibration curve, on the basis of the first peak propagation time obtained with the to-be-inspected piece, a second hardened surface layer depth is calculated using the second calibration curve, on the basis of the second peak propagation time obtained with the to-be-inspected piece, and an estimated value of hardened surface layer depth of the to-be-inspected piece is determined by averaging the first and second hardened surface layer depths.

2. The method according to claim 1, wherein in the calibration curve creation step, in addition to the pairs of samples prepared such that carburization depth varies gradually from pair to pair, a standard sample of the same material having carburization depth 0 is prepared, the standard sample is subjected to the non-destructive test to obtain propagation times of first and second peaks of a first wave of waveform of a signal outputted by the receiver probe receiving a surface wave transmitted from the transmitter probe to propagate along a surface of interest of the standard sample, and a calibration curve is created on the basis of the hardened surface layer depths obtained by the destructive test and a difference between the propagation time obtained with the sample in each pair and the propagation time obtained with the standard sample, and in the hardened layer depth estimation step, the hardened surface layer depth of the to-be-inspected piece is calculated using the calibration curve, on the basis of a difference between the propagation time obtained with the to-be-inspected piece in the propagation time obtaining step and the propagation time obtained with the standard sample.

3. The method according to claim 1, wherein in the waveform measurement step, the waveform of the signal is obtained in the form of a series of points by sampling the signal at a predetermined sampling frequency, wherein each peak is an average of two points on the first wave sampled close to the peak.

4. The method according to claim 1, wherein the calibration curve is approximated by an exponential function whose coefficient of determination is greater than or equal to 0.9.

5. The method according to claim 1, wherein in the propagation time obtaining step as well as the calibration curve creation step, a gate range is set to contain the first and second peaks.

6. An apparatus for measuring depth of a hardened surface layer of a to-be-inspected piece, comprising:

a transmitter probe for transmitting a surface wave to propagate along a surface of interest of the to-be-inspected piece;

a receiver probe for outputting a signal by receiving the surface wave transmitted from the transmitter probe;

a probe moving means for moving the transmitter probe and the receiver probe closer to or farther away from the to-be-inspected piece;

a waveform measurement means for obtaining waveform of the signal outputted by the receiver probe in a non-destructive test performed with the transmitter probe and the receiver probe placed on the surface of interest of the to-be-inspected piece using the probe moving means;

a propagation time obtaining means for obtaining at least propagation time of a first peak of a first wave of the waveform obtained by the waveform measurement means;

a calibration curve creation means for creating a calibration curve on the basis of hardened surface layer depths obtained by a destructive test performed on one of two samples in pairs, and propagation times obtained by the non-destructive test performed on the other of the two samples in pairs, using the wave measurement means and the propagation time obtaining means, the samples in pairs being of a material of which the to-be-inspected piece is made and prepared such that carburization depth gradually varies from pair to pair; and a hardened surface layer depth estimation means for calculating the hardened surface layer depth of the to-be-inspected piece using the calibration curve created by the calibration curve creation means, on the basis of the propagation time obtained with the to-be-inspected piece by the propagation time obtaining means, wherein the calibration curve creation means measures propagation times of first and second peaks of a first wave of waveform of the signal outputted with each sample, respectively, and creates first and second calibration curves on the basis of the hardened surface layer depths and the first peak propagation times and on the basis of the hardened surface layer depths and the second peak propagation times, respectively, and stores the first and second calibration curves in an arithmetic processing device, and the propagation time obtaining means obtains propagation times of first and second peaks of a first wave of the waveform of the signal outputted with the to-be-inspected piece, obtained by the waveform measurement means respectively, and the hardened layer depth estimation means calculates a first hardened surface layer depth using the first calibration curve, on the basis of the first peak propagation time obtained with the to-be-inspected piece, and a second hardened surface layer depth using the second calibration curve, on the basis of the second peak propagation time obtained with the to-be-inspected piece, and determines an estimated value of hardened surface layer depth of the to-be-inspected piece by averaging the first and second hardened surface layer depths.

7. The apparatus according to claim 6, wherein
the calibration curve creating means creates a calibration curve on the basis of the hardened surface layer depths obtained by the destructive test performed on one of the two samples in each pair and a difference between propagation time obtained with the other of the two samples in each pair and propagation time obtained with a standard sample using the waveform measurement means and the propagation time obtaining means, the standard sample being of the same material as the samples in pairs and having carburization depth 0, and
the hardened surface layer depth estimation means calculates the hardened surface layer depth of the to-be-inspected piece using the calibration curve, on the basis of a difference between the propagation time obtained with the to-be-inspected piece using the propagation time obtaining means and the propagation time obtained with the standard sample.

* * * * *